(12) United States Patent
Weide et al.

(10) Patent No.: US 8,114,650 B2
(45) Date of Patent: Feb. 14, 2012

(54) NUCLEIC ACID AND ITS USE EFFECTING CILIATE TETRAHYMENA BIFUNCTIONAL DIHYDROFOLATE REDUCTASE-THYMIDYLATE SYNTHASE DEFICIENCY

(75) Inventors: Thomas Weide, Altenberge (DE); Ulrike Bockau, Münster (DE); Marcus Hartmann, Münster (DE); Lutz Herrmann, Herne (DE)

(73) Assignee: Cilian AG, Muenster (DE)

( * ) Notice: Subject to any disclaimer, the term of this patent is extended or adjusted under 35 U.S.C. 154(b) by 693 days.

(21) Appl. No.: 11/989,717

(22) PCT Filed: Sep. 20, 2006

(86) PCT No.: PCT/EP2006/066545
§ 371 (c)(1),
(2), (4) Date: Apr. 1, 2008

(87) PCT Pub. No.: WO2007/039465
PCT Pub. Date: Apr. 12, 2007

(65) Prior Publication Data
US 2010/0021952 A1    Jan. 28, 2010

(30) Foreign Application Priority Data
Sep. 20, 2005 (EP) .................... 05108663

(51) Int. Cl.
*C07H 21/00* (2006.01)
*C12N 15/00* (2006.01)
*C12P 21/00* (2006.01)
*C12Q 1/26* (2006.01)
*C12Q 1/68* (2006.01)
*C12N 9/02* (2006.01)
*C07K 14/00* (2006.01)

(52) U.S. Cl. ............ 435/189; 435/6.1; 435/25; 435/440; 435/69.1; 530/350; 536/23.2

(58) Field of Classification Search ........... 435/6, 320.1, 435/69, 191, 193; 536/23.2
See application file for complete search history.

(56) References Cited

OTHER PUBLICATIONS

Wheatley, N. D., et al., "Tetrahymena: a Model for Growth, Cell Cycle and Nutritional Studies, with Biotechnological Potential," *BioEssays*, vol. 16, No. 5, May 1994, pp. 367-372.
Schlichtherle, I. M., et al., "Cloning and molecular analysis of the bifunctional dihydrofolate reductase-thymidylate synthase gene in the ciliated protozoan *Paramecium tetraurelia*," Mol-Gen Genet (1996) vol. 250, No. 6, pp. 665-673.
Bifunctional dihydrofolate reductase-thymidylate synthase (DHFR-TS) [Includes: Dihydrofolate reductase (EC 1. 5. 1. 3); Thymidylate synthase (EC 2.1. 1.45)] retrieved from Database UniProt [Online] Nov. 1, 1996.
Bzik, J. D., et al., "Molecular cloning and sequence analysis of the *Plasmodium falciparum* dihydrofolate reductase-thymidylate synthase gene," *Proc. Natl. Acad. Sci USA*, vol. 84, No. 3, pp. 8360-8364, Dec. 1987.
Eldin De Pecoulas P. et al., "Analysis of the *Plasmodium vivax* dihydrofolate reductase-thymidylate synthase gene sequence," *Gene: An International Journal on Genes and Genomes*, Elsevier, vol. 211, No. 1, pp. 177-185, Apr. 28, 1998.

*Primary Examiner* — Delia Ramirez
(74) *Attorney, Agent, or Firm* — Jacobson Holman PLLC

(57) ABSTRACT

A method for producing a ciliate cell with reduced or essentially no dihydrofolate reductase (DHFS) activity or reduced or essentially no thymidylate synthase (TS) activity or both reduced or essentially no dihydrofolate reductase and thymidylate synthase (DHFR-TS) activity is claimed, comprising the steps of
a) transforming ciliate cells by inserting a construct containing an allele altering the gene encoding the endogenous DHFR-TS into at least one of the endogenous DHFR-TS genes of the ciliate macronucleus (MAC),
b) inducing an allelic assortment process in the transformed ciliate cells to generate cells having the construct inserted in most or all functional DHFR-TS genes of the MAC, and
c) identifying the cells generated in step b) by cultivation with or without thymidine.

11 Claims, 11 Drawing Sheets

Figure 10:
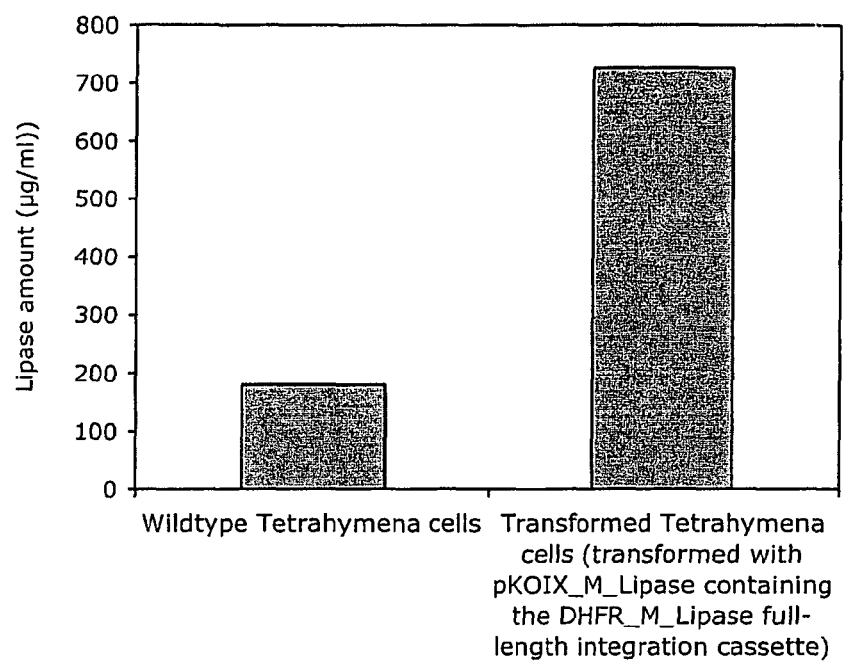

Figure 1: Genomic structure of *T. thermophila* DHFR-TS bifunctional enzyme
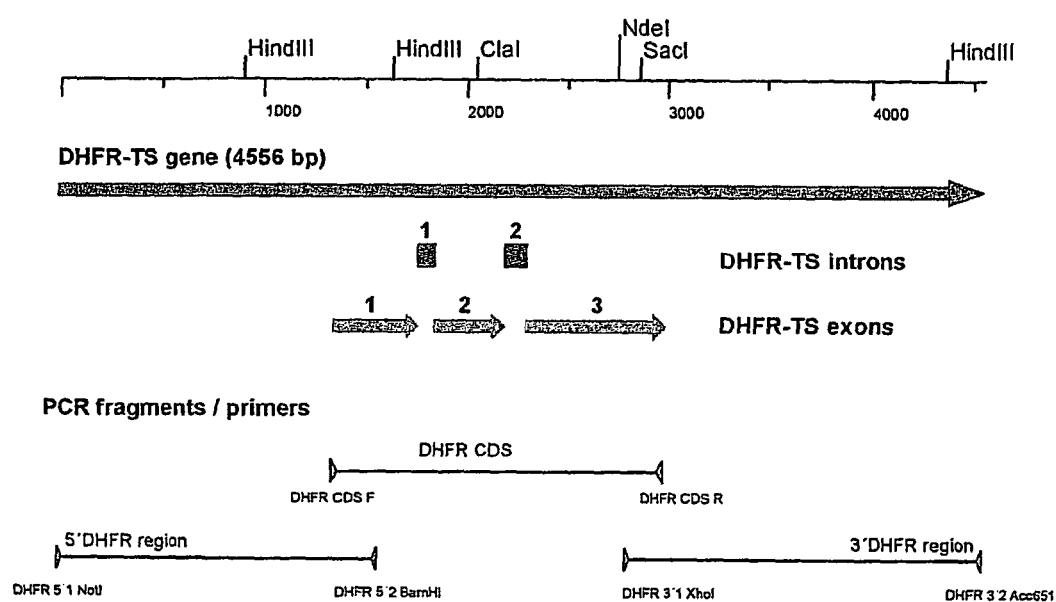

Figure 2: pKOI: DHFR-TS knockout construct
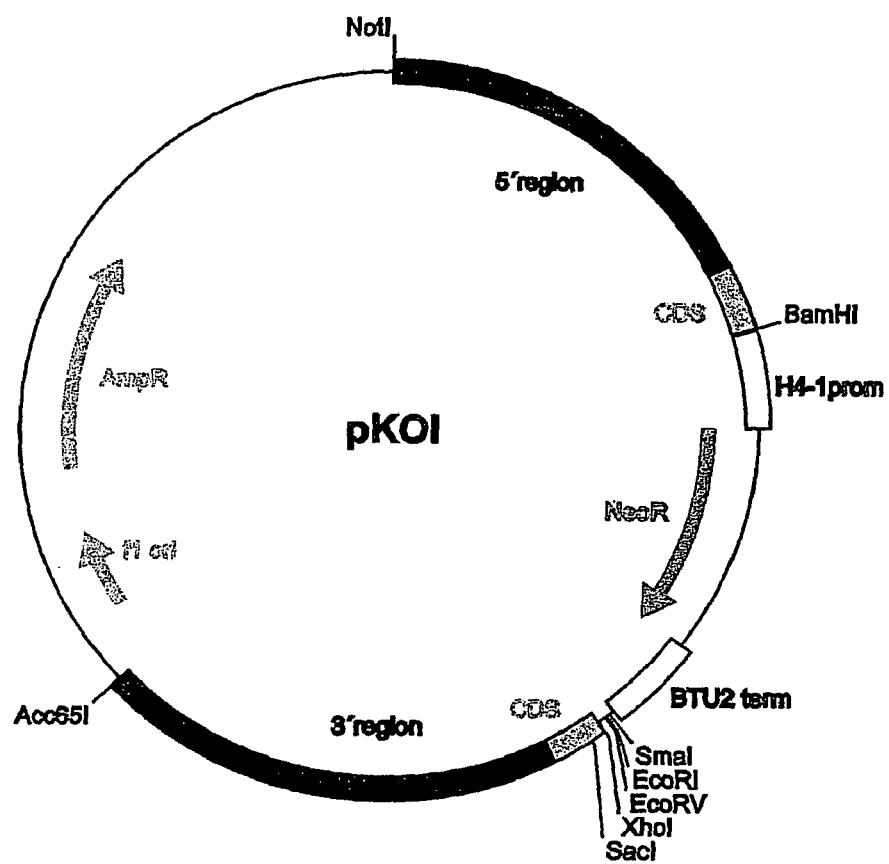

Figure 3: Generation of DHFR-TS deficient strains by allelic assortment
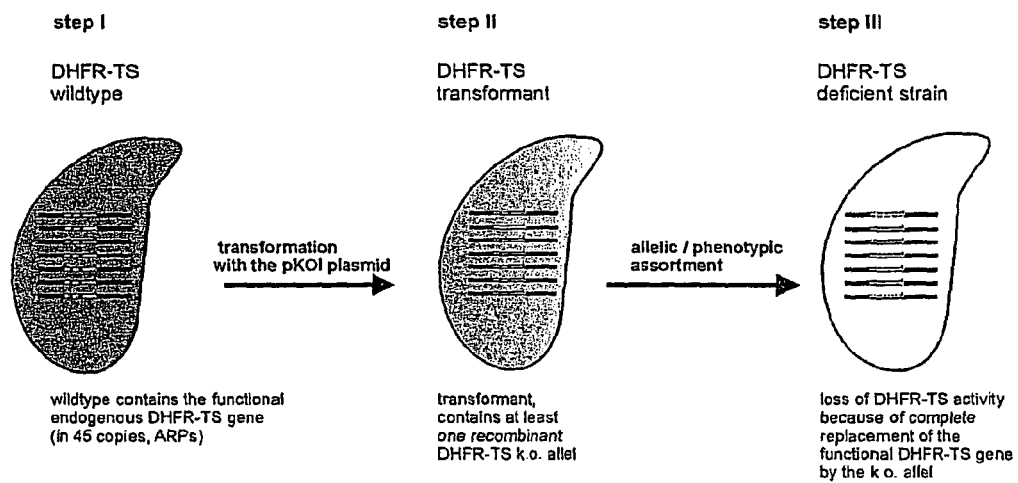

Figure 4: Selection of DHFR-TS knock out cells by growth on thymidine
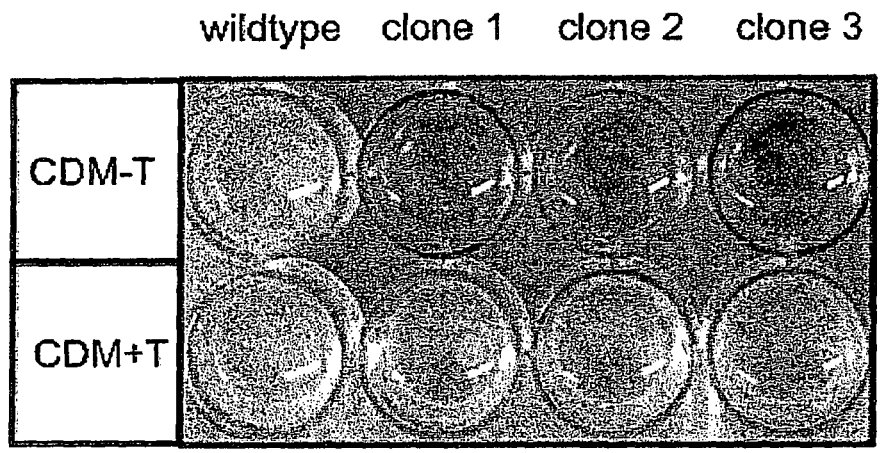

Figure 5: Growth of DHFR-TS deficient *Tetrahymena* compared to wildtype
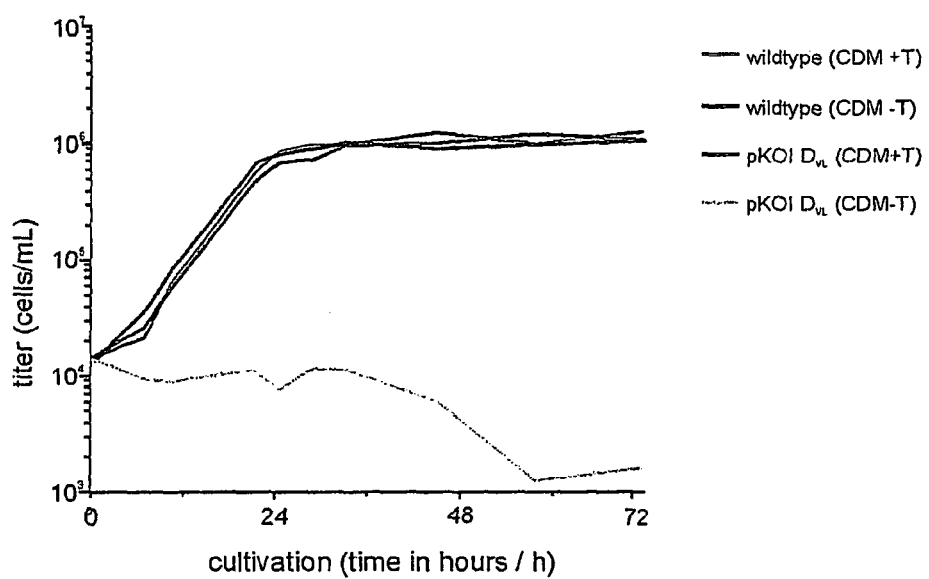

Figure 6: Proper integration of DHFR-TS knock out construct
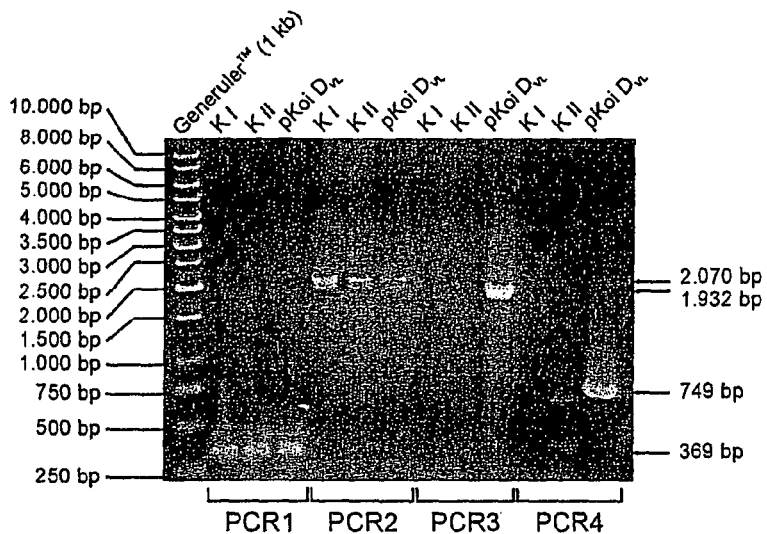
DHFR-TS gene sructure
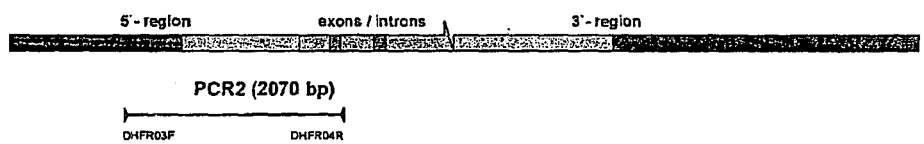
pKOI DvL plasmid
DHFR-TS knock out by knock in (integration)
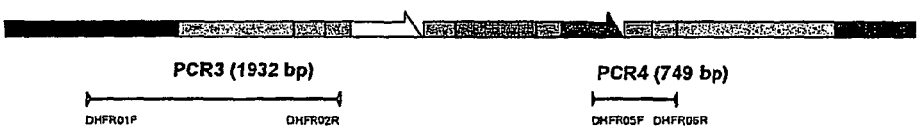

Figure 7: Enzyme function of knock in target
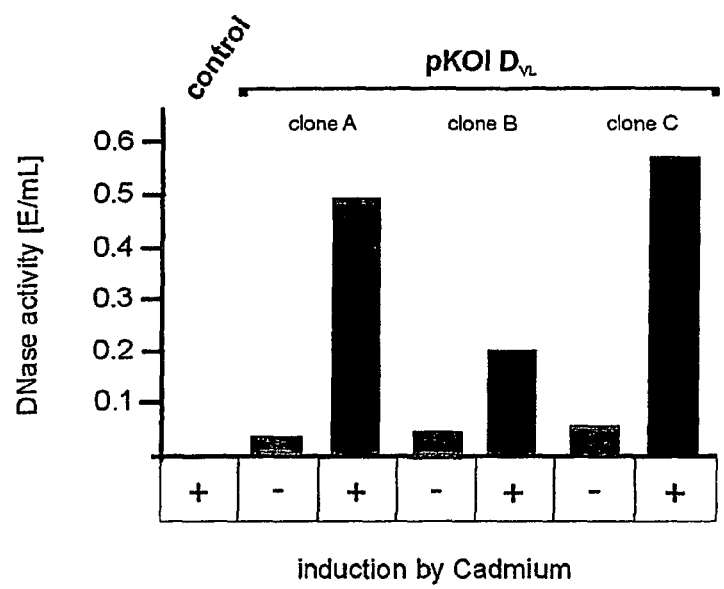

Figure 8: Expression of knock in target.
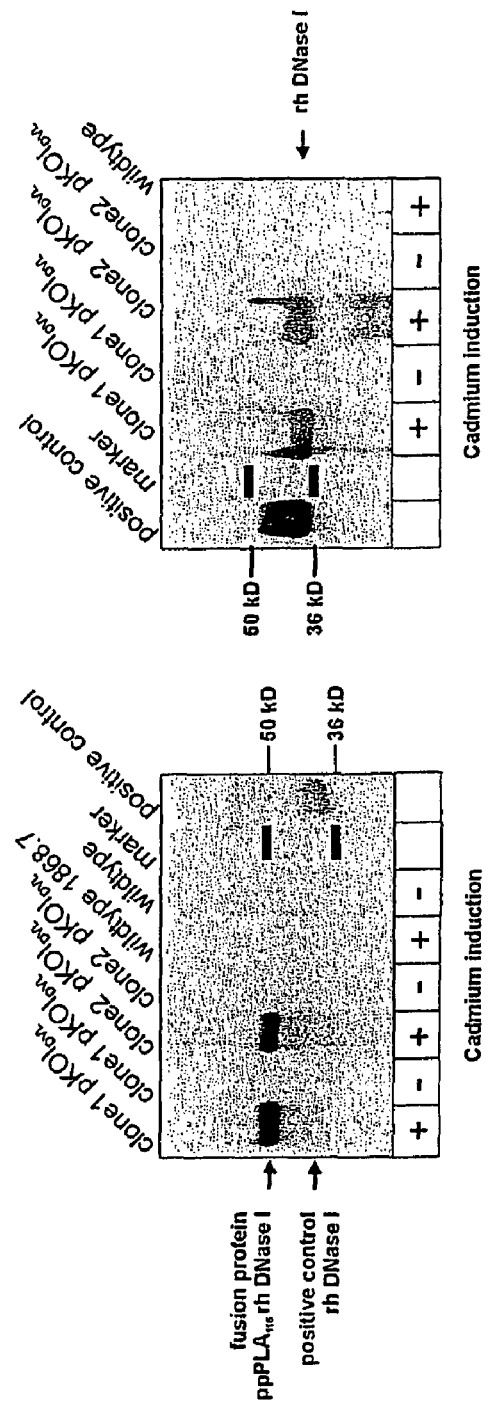

Figure 9: Overview of the reconstitution of DHFR-TS activity by knock in
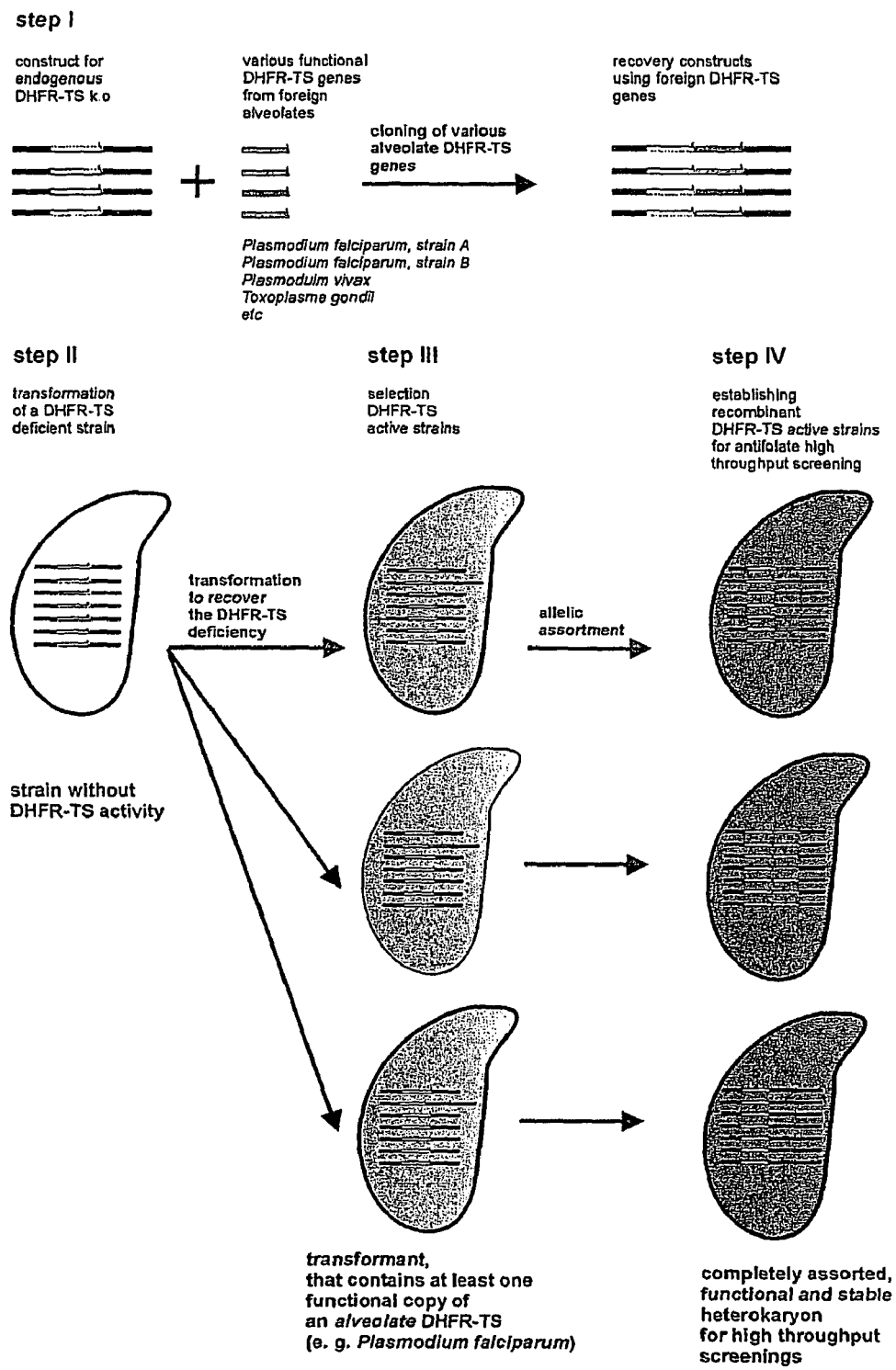

US 8,114,650 B2

SEQUENCE LISTING

```
<160> NUMBER OF SEQ ID NOS: 3

<210> SEQ ID NO 1
<211> LENGTH: 4556
<212> TYPE: DNA
<213> ORGANISM: Tetrahymena thermophila
<220> FEATURE:
<221> NAME/KEY: 3'UTR
<222> LOCATION: (1)..(1760)
<220> FEATURE:
<221> NAME/KEY: CDS1
<222> LOCATION: (1346)..(1760)
<220> FEATURE:
<221> NAME/KEY: Intron
<222> LOCATION: (1761)..(1839)
<220> FEATURE:
<221> NAME/KEY: CDS2
<222> LOCATION: (1840)..(2190)
<220> FEATURE:
<221> NAME/KEY: Intron
<222> LOCATION: (2191)..(2302)
<220> FEATURE:
<221> NAME/KEY: 5'UTR
<222> LOCATION: (2995)..(4556)

<400> SEQUENCE: 1
acagagttaa tggaaatgga gctatgattg tcagtccttc tcgtgttcct cagagaggtg     60
gtgctattgg aactagacag aacttacctg atactatgta gcatattttc gctacaaacc    120
```

```
attaaatata acagccccag acagtagaag atttgcaaag aatggaagaa atataaagaa      180
atatagaaaa cgaaaacaat atttatagta ataatccca taataatata gaaaatccag       240
agaatgaaaa ttaggaatcg cgagtaaact aagttcctac tttcctataa aacaactaat      300
tttaaataaa caacatttct gataaaaaaa aatgagctaa ttgacaacct cgcctatcta      360
caaacaaata agttgtatta gctaattatt ctttacttac tcttctacta aaattttaat     420
ctaataaata aatttatata atcaaaaaca attttcttga tctgaagtaa atagcatgtc     480
cgccacctct aaaaataatc aaaataaaaa atacataaaa tttaagcaaa ttcaaaaaaa     540
ttcttaaaaa aaagaatgaa tgaatgaatg aagatggata caaagagcta tcaaaaaaga     600
aataactaat agaataattt attaaaatct ataaaatcat agatctaatt ccagtttttt     660
tcttctacga aagtgaaagt tagttttata agattgatag aaagatattt gtatctatta     720
gcattaaaat agaattaaga tcttctaaga tattctctat ccctaccta tacctctctt      780 ttactaatat acctataata aataacatct acttattaat ttatgatact ccttttattc     840
aaaattatta actaaaataa aaatttatta cagaaatctt acttttaaat tctaaaagtt     900
aagcttctaa ttactattaa ataaataaat aatatatatt tatcttgtat tttgtaaaaa     960
tatttcactt ttattgccat ttcagttcat tctatttatt catttctata cttttgcta    1020 ttaacttaat aaaatatatt ttatactatg aaaatttact tgttaagtt gagagaattt    1080 aattcttttt ataaaaaatc tatcttgaga ttactctagt atcatctaaa aatcaaaaat    1140
agctatttat aatttattgg cgcaatcctt aaaagatcgc gggtatatg aatcactaac    1200 tcattcactg gcttgcatcg cttaactttg aatttagctt atatatccgc tatattttta    1260
caaatcaaat tttaatttat aaaataagtg aaaagtaaat tgaaattaaa aatagaaatt    1320
taacaaataa acagactcag tataaatgaa aacaagacat tttgatatag ttttagctta    1380
gactttaaaa aaatagggta taggttataa gaacagttta ccatggagac tacctaatga    1440
gcttaaaaac tttaaaaaaa taactacaga aactaagaac aaaggcctat aaaacgctgt    1500
tatcatgggt aaaaatactt gggaagcact acctaaaaag caataaccat tgaaagatcg    1560
cttaaatatt gttatttcca ctactatgca agaggggtaa attgcagatc attcctacgc    1620
ctgtaaaagc ttagattctg cttttaaactt tttagaatag taaaattaaa tataagatgc    1680
ccttgtaatt ggaggagcta aactttgcca ataagcatta agcgatcaga acttagata     1740 gattcatcta acaagagtag gtcagtagaa ttaaatttat taaatacttt ctttttatga    1800 acaaagaga taattaaata acttttcaaa aatatttagg tgtcgaagtt gagtgcgatg     1860 ttttttatgca aaaggactac ttaaaaaact ttgatatgat tgaggtgtct gaaacttaaa    1920
gcgaaaataa tttaaattat gattttacta ggtatttaa taagaattat aaaggataag    1980 ttgaccttc tctctttaag aaaatgtaca agcctcatca agaatattaa tacttagaac    2040
ttatcgatga aattataaag aatggacatg ttaaaacaga cagaactgga actggtacaa    2100
tttctcagtt tggcaagttg atgagatttg acttatcaaa gagttttcct ctgcttacta    2160
ccaaaaatgt tttttggaga ggtgtagtag aagtaataaa tatatttatt tatttattaa    2220
tttatagttt gatagattta aaaatgaaat ttagtctgat ttttagtaga ataaataaaa    2280
taatctaaat atataaatta ataggaactt atttggttta tcaaaggcag tacaaacagc    2340
aaaatacttt cagaaaaagg agttaaaata tgggacggta atggcagcag agaattttta    2400
gattaattag gctttaaaaa cagagaagaa ggagatttag gtcctgttta tggtttctaa    2460
tggagacact tcggtgctga atataaagat atgcatacaa attataaagg taaaggtgtc    2520
```

-continued

| | |
|---|---|
| gaccagcttc aagatttaat taacacaata aagaaaaatc ctgacagcag aaggatgatt | 2580 |
| atgaatgcct ggaatgttaa agatctacca ttgatggctt tacctccttg tcatgtcatg | 2640 |
| agctagtttt atgtaaatga taataaacta agctgtatga tgtactaaag atcttgtgat | 2700 |
| atgggtttag gaataccatt taatatagcc agttatgctt tattgactca tatgatagct | 2760 |
| taagtcacta atatgtaagt tggagagttt atacatgttc taggtgatgc tcatgtttac | 2820 |
| tctaatcacg tagattaact aaaaatttaa ttagaaagag ctccataccc cttccctctt | 2880 |
| ttaaaaatta ataacaacaa gtaatataac tctattgaag acttcactct tgaagatttc | 2940 |
| gaattaattg gatacaacta tcaccctaaa atataaatga aaatggctgt ctgaaatgat | 3000 |
| taaagactta tatattttgg ataatcttac tactaaaata ctaactaact taaatggtta | 3060 |
| tatacaataa atctatctta ataagctatt ttaaatttta aatcaatcgt tcaattcttt | 3120 |
| attttataaa ctttcaaatc attatcaagc aaattttaaa taaatatttt tttttatat | 3180 |
| attgttgaac ttttgttcag cctgaatggc atagagctaa gtaattgtaa agttgaaaca | 3240 |
| ttaaaaatca aaattcaata gaaaatttgg aaaagaatt ttttatttag ttagaaataa | 3300 |
| aacaaattat ttatataatt ttttatagtt gattgatata tttatttatt taatttcata | 3360 |
| tttagagtga gcataatctt aggcacttta aaagctaagc tctaattaat tttagatttt | 3420 |
| atttgaatct ttatattata aaaatattaa atattattgt agaaaataga atttaattac | 3480 |
| tgaataggca tctttataga ttataatttt ctaaactttc tgattttgtt tgatatattt | 3540 |
| attaaatgat cataatttac ctaattatgt ctataaatag agtaaaaata tcattttta | 3600 |
| agagtaataa tttactataa gtcaatctat aatccaacta aacttggtaa tttactcaaa | 3660 |
| ttttcaataa gttcttatac ttaatcattt cctaaatggc aattactaat tattattttg | 3720 |
| taatgaaaat taaatatata taataaaaatc actaattaat ttaccttaaa cctaaattta | 3780 |
| aatattttaa acagctgaat tgagtgagta tagaagctat cgacaaaaca cattctttac | 3840 |
| atccaatatt atcactgttg ttttatattt tataatttaa ataaaaatct tataaaacaa | 3900 |
| tttaattaat tttactctaa attaaattat agtttattta attgattaaa tctacatagc | 3960 |
| tactctttaa aagcctgtgc ataactagtg cctatataat tataccatc aataatttaa | 4020 |
| ttttttagtaa ttataattaa ataagaattt actataattg aagggtaagg tttctaatag | 4080 |
| actaaaattc ggtaagtcca tttatgatat tattcaatga tttctaggag agagaacatt | 4140 |
| tacttaataa tatttaacag attaatttta aatcttttt aaaaaattct actttaatga | 4200 |
| taagtttaat tcagatagct acttacagaa attaactgtg tttattgaca attcttaatt | 4260 |
| aaattctatt ttatttttcac taatttaata aaaaaaatag ctaaaaataa aattttaat | 4320 |
| taaaataatt atactccaaa actagttcta gcttttttaa gctttaaaat tcacttaaat | 4380 |
| attcaaatac ttaagatata tctccttcta ctctattttt acttaataga ataattttta | 4440 |
| tatcataact cttaaaaact aaaattacct caacaaaaac gttagatttt caagatattg | 4500 |
| attttatttt agcttcaaaa aaaagtatta aagcccttct ttgcttattt aattgt | 4556 |

<210> SEQ ID NO 2
<211> LENGTH: 1458
<212> TYPE: DNA
<213> ORGANISM: Tetrahymena thermophila

<400> SEQUENCE: 2

| | |
|---|---|
| atgaaaacaa gacattttga tatagtttta gcttagactt taaaaaaata gggtataggt | 60 |
| tataagaaca gtttaccatg gagactacct aatgagctta aaaactttaa aaaaataact | 120 |

-continued

```
acagaaacta agaacaaagg cctataaaac gctgttatca tgggtaaaaa tacttgggaa      180
gcactaccta aaaagcaata accattgaaa gatcgcttaa atattgttat ttccactact      240
atgcaagagg ggtaaattgc agatcattcc tacgcctgta aaagcttaga ttctgcttta      300 aacttttag aatagtaaaa ttaaatataa gatgcccttg taattggagg agctaaactt       360
tgccaataag cattaagcga tcagagactt agatagattc atctaacaag agtaggtgtc     420
gaagttgagt gcgatgtttt tatgcaaaag gactacttaa aaaactttga tatgattgag     480
gtgtctgaaa cttaaagcga aaataattta aattatgatt ttactaggta ttttaataag    540
aattataaag gataagttga cccttctctc tttaagaaaa tgtacaagcc tcatcaagaa     600
tattaatact tagaacttat cgatgaaatt ataaagaatg gacatgttaa aacagacaga     660
actggaactg gtacaatttc tcagtttggc aagttgatga gatttgactt atcaaagagt    720
tttcctctgc ttactaccaa aaatgttttt tggagaggtg tagtagagga acttatttgg    780
tttatcaaag gcagtacaaa cagcaaaata ctttcagaaa aaggagttaa aatatgggac    840
ggtaatggca gcagagaatt tttagattaa ttaggcttta aaaacagaga agaaggagat    900
ttaggtcctg tttatggttt ctaatggaga cacttcggtg ctgaatataa agatatgcat    960
acaaattata aaggtaaagg tgtcgaccag cttcaagatt taattaacac aataaagaaa    1020
aatcctgaca gcagaaggat gattatgaat gcctggaatg ttaaagatct accattgatg    1080
gctttacctc cttgtcatgt catgagctag ttttatgtaa atgataataa actaagctgt    1140
atgatgtact aaagatcttg tgatatgggt ttaggaatac catttaatat agccagttat    1200
gctttattga ctcatatgat agcttaagtc actaatatgt aagttggaga gtttatacat    1260
gttctaggtg atgctcatgt ttactctaat cacgtagatt aactaaaaat ttaattagaa    1320
agagctccat accccttccc tcttttaaaa attaataaca acaagtaata taactctatt    1380
gaagacttca ctcttgaaga tttcgaatta attggataca actatcaccc taaaatataa    1440
atgaaaatgg ctgtctga                                                  1458
```

<210> SEQ ID NO 3
<211> LENGTH: 485
<212> TYPE: PRT
<213> ORGANISM: Tetrahymena thermophila

<400> SEQUENCE: 3

```
Met Lys Thr Arg His Phe Asp Ile Val Leu Ala Gln Thr Leu Lys Lys
  1               5                  10                  15

Gln Gly Ile Gly Tyr Lys Asn Ser Leu Pro Trp Arg Leu Pro Asn Glu
             20                  25                  30

Leu Lys Asn Phe Lys Lys Ile Thr Thr Glu Thr Lys Asn Lys Gly Leu
         35                  40                  45

Gln Asn Ala Val Ile Met Gly Lys Asn Thr Trp Glu Ala Leu Pro Lys
     50                  55                  60

Lys Gln Gln Pro Leu Lys Asp Arg Leu Asn Ile Val Ile Ser Thr Thr
 65                  70                  75                  80

Met Gln Glu Gly Gln Ile Ala Asn His Ser Tyr Ala Cys Lys Ser Leu
                 85                  90                  95

Asn Ser Ala Leu Asn Phe Leu Glu Gln Gln Asn Gln Ile Gln Asp Ala
            100                 105                 110

Leu Val Ile Gly Gly Ala Lys Leu Cys Gln Gln Ala Leu Ser Asp Gln
        115                 120                 125

Arg Leu Arg Gln Ile His Leu Thr Arg Val Gly Val Glu Val Glu Cys
    130                 135                 140
```

```
Asn Val Phe Met Gln Lys Asp Tyr Leu Lys Asn Phe Asp Met Ile Glu
145                 150                 155                 160

Val Ser Glu Thr Gln Ser Glu Asn Asn Leu Asn Thr Asp Phe Thr Arg
            165                 170                 175

Tyr Phe Asn Lys Asn Tyr Lys Gly Gln Val Asp Pro Ser Leu Phe Lys
                180                 185                 190

Lys Met Tyr Lys Pro His Gln Glu Tyr Gln Tyr Leu Glu Leu Ile Asp
                195                 200                 205

Glu Ile Ile Lys Asn Gly His Val Lys Thr Asp Arg Thr Gly Thr Gly
            210                 215                 220

Thr Ile Ser Gln Phe Gly Lys Leu Met Arg Phe Asp Leu Ser Lys Ser
225                 230                 235                 240

Phe Pro Leu Leu Thr Thr Tyr Asn Val Phe Trp Arg Gly Val Val Glu
                245                 250                 255

Glu Leu Ile Trp Phe Ile Lys Gly Ser Thr Asn Ser Lys Ile Leu Ser
                260                 265                 270

Glu Lys Gly Val Lys Ile Trp Asp Gly Asn Gly Ser Arg Glu Phe Leu
            275                 280                 285

Asp Gln Leu Gly Phe Lys Asn Arg Glu Glu Gly Asp Leu Gly Pro Val
            290                 295                 300

Tyr Gly Phe Gln Trp Arg His Phe Gly Ala Glu Tyr Lys Asp Met His
305                 310                 315                 320

Thr Asn Tyr Lys Gly Lys Gly Val Asp Asn Leu Asn Asp Leu Ile Asn
                325                 330                 335

Thr Ile Lys Lys Asn Pro Asp Ser Arg Arg Met Ile Met Asn Ala Trp
                340                 345                 350

Asn Val Lys Asp Leu Pro Leu Met Ala Leu Pro Pro Cys His Val Met
            355                 360                 365

Ser Gln Phe Tyr Val Asn Asp Asn Lys Leu Ser Cys Met Met Tyr Gln
            370                 375                 380

Arg Ser Cys Asp Met Gly Leu Gly Ile Pro Phe Asn Ile Ala Ser Tyr
385                 390                 395                 400

Ala Leu Leu Thr His Met Ile Ala Gln Val Thr Asn Met Gln Val Gly
                405                 410                 415

Glu Phe Ile His Val Leu Gly Asp Ala His Val Tyr Ser Asn His Val
                420                 425                 430

Asp Gln Leu Lys Ile Gln Leu Glu Arg Ala Pro Tyr Pro Phe Pro Leu
            435                 440                 445

Leu Lys Ile Asn Asn Asn Lys Gln Tyr Asn Ser Ile Glu Asp Phe Thr
    450                 455                 460

Leu Glu Asp Phe Glu Leu Ile Gly Tyr Asn Tyr His Pro Lys Ile Gln
465                 470                 475                 480

Met Lys Met Ala Val
                485
```

NUCLEIC ACID AND ITS USE EFFECTING CILIATE TETRAHYMENA BIFUNCTIONAL DIHYDROFOLATE REDUCTASE-THYMIDYLATE SYNTHASE DEFICIENCY

This is a 371 of PCT/EP2006/066545 filed on Sep. 20, 2006.

FIELD OF THE INVENTION

The present invention addresses fields of recombinant molecular biology, in particular the use of a bifunctional marker enzyme in *Tetrahymena* enabling selection of transformands and facilitating drug discovery in parasitic Protozoa research.

BACKGROUND OF THE INVENTION

*Tetrahymena* is a ciliated eukaryotic unicellular organism belonging to the regnum of Protozoa and bearing two nuclei, a transcriptionally silent, diploid germline micronucleus (MIC) and a transcriptionally active, polyploid somatic macronucleus (MAC). In 1923, when Nobel Laureate Andre Lwoff succeeded in growing *Tetrahymena* in pure culture, the basis for exploiting this alveolate as a model organism was laid. Milestone discoveries made in *Tetrahymena* are the discovery of dynein motors, telomeres, RNA-mediated catalysis, telomerase and the function of histone acetyltransferases in transcription regulation. Within the last decades molecular biological techniques have been developed to alter *Tetrahymena's* genome and proteome: DNA transfection methods comprise inter alia microinjection into the MAC by electroporation and biolistic bombardment of MIC and MAC. Episomal plasmids based on an rDNA-replicon are available, as well as knock-out/-in techniques based on homologous recombination. On protein level, heterologous expression of related species has been performed and also endogenous proteins were silenced by a novel antisense-ribosome-technique. The advantages of using *Tetrahymena* in biotechnological applications include fast growth, high biomass, fermentation in ordinary bacterial/yeast equipment, up-scalability as well as existence of cheap and chemically defined media.

So far, only a few markers that can be used in *Tetrahymena* have been described: ribosomal point mutation mediated resistances, a plasmid based neomycin resistance and a complicated beta-tubulin selection marker making use of an inducible promotor in combination with mutated tubulins being resistant/sensitive to the mitotic drug taxol[1]. Yet no true auxotrophic marker is available that permits selection without the use of antibiotics or drugs. This is where the present invention applies.

DESCRIPTION OF THE INVENTION

Critical enzymes in pyrimidine biosynthesis are the enzymes dihydrofolate reductase (DHFR) and thymidylate synthase (TS). DHFR catalyses the production of tetrahydrofolate from dihydrofolate; TS is in charge of transferring a methyl-group from $N^5$, $N^{10}$-methylene-tetrahydrofolate to dUMP thereby generating dTMP and tetrahydrofolate. These enzymes being crucial for pyrimidine synthesis have been used as auxotrophic markers in various systems by targeted gene disruption, but also a number of inhibitors (antifolates) have been developed as anti parasite drugs. In animals, fungi and eubacteria the DHFR and TS gene are separately translated, whereas plants, Alveolata and Euglenozoa have a bifunctional fusion gene with both enzyme activities combined in one protein ("DHFR-TS").

The occurrence of the bifunctional enzyme in *Tetrahymena pyriformis* has been postulated in 1984[2] and 1985[3] but no functional or even molecular biological analysis had been performed. A partial amino acid sequence of DHFR-TS of a non determined "*T. pyriformis*-like strain" has been published in 2001[4], but this work is lacking any proof of linkage of the described partial cDNA to enzyme function.

The present invention provides a detailed characterization of the *T. thermophila* DHFR-TS gene including gene structure and functional data on the enzyme including data on in vivo function. In addition to a simple auxotrophic marker that is described for the first time in ciliates, the combination of these results with certain uncommon properties of *Tetrahymena* yields a surprisingly powerful tool for development and discovery of new antifolates against parasitic apicomplexans like for example *Plasmodium* sp. (malaria), *Toxoplasma gondii* (toxoplasmosis) and *Cryptosporidium* sp. (cryptosporidiosis).

Great efforts are being made to fight these most severe worldwide problems by targeting the DHFR-TS of the above mentioned parasites by antifolates. Initial success in the fight against malaria has been overcome by the rise of drug resistant *Plasmodium* strains. Especially in the case of malaria the diversity of DHFR-TS is manifold due to the occurrence of different strains (*P. falciparum, P. vivax, P. malariae, P. ovale*) and high frequency of DNA-recombination/-mutations producing new resistances over and over again. By revealing the crystal structure of the mutated and thereby resistant DHFR-TS enzymes, new small molecule drugs are being developed by computer aided molecular modelling. The major problem is the testing of the drug candidates for efficacy: As endoparasites are difficult to culture and have an unusual complex life cycle direct testing of the new compounds is nearly impossible. A detour has been described, that makes use of dhr1 gene deficient yeast strains[5] expressing the functional, parasitic DHFR-TS enzyme of interest thereby reconstituting the dhr1 deficiency. However this approach has a lot of disadvantages: The codon usage of parasitic apicomplexans, is very different from all commonly used expression-systems like *E. coli*, yeast and mammalian cell-lines and some tRNAs needed for translation are not abundant in these model organisms. Apicomplexa/Sporozoa, belonging to the phylogenetic group of Alveolata, possess a number of special cell biological features, the most notable being the presence of cortical alveoli, flattened vesicles packed into a continuous layer supporting the membrane. No model organism described so far has this assortment of special properties that will influence drug uptake and virtue.

All the problems mentioned above can be overcome by the use of *Tetrahymena*:

It belongs to the Alveolata and is the most closely related species to apicomplexans. *Tetrahymena* is capable of growing in chemical defined media without the presence of thymidine arguing for a functional salvage pathway for dTMP synthesis by a bifunctional DHFR-TS enzyme. Deficiency in this enzyme activity should yield cell lines that only grow in media supplemented with thymidine. To destroy DHFR-TS activity various common techniques can be used like e.g. targeted gene knockout, site directed mutagenesis of essential amino acids and random mutagenesis. Screening for DHFR-TS deficient clones can be performed by replica plated culturing in media with (T+) or without thymidine (T−). Potential clones should only grow in T+ but not in T−. Successful reconstitution of enzyme activity can be achieved by transforming aforementioned cells with DNA fragments encoding for a functional DHFR-TS enzyme yielding cells that will grow on T−. This method allows selection of transformands without using drugs or antibiotics. In case of the exogenous, recombinant DHFR-TS being derived from parasitic apicomplexans an ideal model system for antifolate drug screening is achieved that can readily be used in a high throughput system.

A method for producing a ciliate cell with reduced or essentially no dihydrofolate reductase (DHFS) activity or reduced or essentially no thymidylate synthase (TS) activity or both reduced or essentially no dihydrofolate reductase and thymidylate synthase (DHFR-TS) activity is claimed, comprising the steps of a) transforming ciliate cells by inserting a construct containing an allele altering the gene encoding the endogenous DHFR-TS into at least one of the endogenous DHFR-TS genes of the ciliate macronucleus (MAC),
b) inducing an allelic assortment process in the transformed ciliate cells to generate cells having the construct inserted in most or all functional DHFR-TS genes of the MAC, and
c) identifying the cells generated in step b) by cultivation with or without thymidine.

The method according to the invention can also utilize the fact that the micronucleus (MIC) stores the genetic information for sexual progeny. Consequently the method according to the invention also encompasses that in step a) the construct containing an allele altering the gene encoding the endogenous DHFR-TS is inserted into at least one of the endogenous DHFR-TS genes of the ciliate micronucleus (MIC), and in step b) the cells having the construct inserted in most or all functional DHFR-TS genes of the MAC are generated by breeding the cells of step a) with other ciliate cells to produce progeny that contains a new MAC derived from the altered MIC.

According to the invention it can be preferred that the ciliate is *Tetrahymena*, preferably *Tetrahymena thermophila*.

The DHFR-TS gene according to the invention can have a nucleotide sequence according to Seq ID No. 1.

It may be preferred that the region 1.5 kb up- and downstream of the cell's endogenous gene coding for the DHFR-TS bifunctional enzyme is additionally altered.

The method according to the invention can comprise an additional step of reconstituting the DHFR-TS activity by transfection of the cells with a DNA or RNA molecule coding for a functional non-endogenous DHFR-TS enzyme.

The term "non-endogenous" means that the DNA or RNA molecule is derived from a different organism, preferably from a different alveolate species.

Furthermore the method according to the invention can comprise an additional step of reconstituting the DHFR-TS activity by transfection of the cells with a DNA or RNA molecule coding for a functional endogenous DHFR-TS enzyme as well as another protein.

The DNA or RNA molecule coding for a functional endogenous or non-endogenous DHFR-TS enzyme can be derived from an alveolate, preferably a ciliate, even more preferably from *Tetrahymena* and most preferably from *Tetrahymena thermophila*. It may also be derived from an apicomplexan.

Furthermore the DNA or RNA molecule coding for a functional DHFR-TS enzyme can be represented by Seq. ID No. 1 and the amino acid sequence of the enzyme can be represented by Seq. ID No. 3.

The present invention also comprises a ciliate cell with an auxotrophy for thymidine. Preferably the ciliate cell according to the invention has reduced or essentially no DHFR activity or reduced or essentially no TS activity or both reduced or essentially no DHFR-TS activity. Said ciliate cell may be obtainable by using the methods as described herein.

A ciliate cell with reconstituted DHFR-TS activity is also disclosed, whereby the DHFR-TS enzyme is not the endogenous form. Said ciliate cell may be obtainable by using the methods as described herein.

Furthermore the present invention encompasses a ciliate cell with reconstituted endogenous DHFR-TS activity expressing another protein. Said ciliate cell may be obtainable by using the methods as described herein.

The use of the ciliate cells according to the present invention having a reconstituted non-endogenous DHFR-TS enzyme activity in an assay to detect chemical compounds affecting DHFR-TS enzyme activity is also claimed, comprising the steps of a) bringing the cells into contact with the compound to be tested,
b) measuring the DHFR-TS enzyme activity of the cells, and
c) comparing the DHFR-TS enzyme activity to the DHFR-TS enzyme activity of control cells.

The ciliate cells according to the invention having a reconstituted endogenous DHFR-TS enzyme activity can be used for the production of another protein.

An isolated nucleic acid coding for the DHFR-TS protein having the nucleotide sequence according to Seq ID No.1 and an isolated DHFR-TS protein having the amino acid sequence according to Seq ID No. 3 is also within the scope of the present invention.

FIG. 1: Genomic structure of *T. thermophila* DHFR-TS bifunctional enzyme

The DHFR-TS gene structure of *T. thermophila* consists of three exons (grey) and 2 introns (black). Primer pairs to amplify DNA for homologous integration and to amplify the CDS or cDNA are shown in the bottom part.

FIG. 2: pKOI: DHFR-TS knockout construct

FIG. 2 shows the knockout construct used for a targeted knockout of the DHFR-TS gene in *T. thermophila*. It consists of 3' and 5' flanking regions of the *T. thermophila* DHFR-TS gene and parts of its coding sequence (CDS), disrupted by a functional neomycin cassette conferring resistance to paromomycin.

FIG. 3: Generation of DHFR-TS deficient strains by allelic assortment

Wildtype strains are transfected with pKOI. In one copy of the 45 ARPs the endogenous DHFR-TS gene is substituted by the knock out construct (step 2). By amitotic division of the MAC and high selection pressure clones will arise that have sorted out all endogenous DHFR-TS genes and retain only recombinant and defect DHFR-TS genes (step 3).

FIG. 4: Selection of DHFR-TS knockout cells by growth on thymidine

*Tetrahymena* cells with disrupted DHFR-TS gene (clone 1-3) do not grow without the presence of thymidine (CDM−T), whereas wildtype cells do. Addition of thymidine to the medium (CDM+T) recovers growth.

FIG. 5: Growth of DHFR-TS deficient *Tetrahymena* compared to wildtype

Growth kinetics of DHFR-TS knock out cells compared to wildtype cells in media with or without thymidine show that the knock out strain (pKOI) is growing as fast as wildtype cells on thymidine supplemented media (CDM+T). Knock out cells die without thymidine present (CDM−T). The curves are calculated by mean values of at least three independent experiments.

FIG. 6: Proper integration of DHFR-TS knockout construct

This figure points up the PCR approach to determine that the knock out/-in construct has integrated into the DHFR-TS gene locus.

Three different cells were tested: K1 is a wildtype control, K2 are cells transfected with a plasmid carrying only the disrupting cassettes but no DHFR-TS gene sequences and pKOI $D_{VL}$ are cells transformed with the pKOI $D_{VL}$ plasmid. PCR1 is a control reaction amplifying 369 bp of the beta-hexosaminidase gene. PCR2 is to detect endogenous DHFR-TS (note that in the pKOI $D_{VL}$ cells there still is a wildtype gene in the MIC!). PCR3 only yields PCR-product for correctly integrated pKOI $D_{VL}$ DNA. PCR4 shows that the full-length expression cassette has integrated.

FIG. 7: Enzyme function (DNase) of knock in target

Supernatants of three clones transformed with pKOI $D_{VL}$ were assayed for DNase activity. Only induced cells (+) show high levels of DNase activity. Transformed, but uninduced cells show a slightly elevated enzyme activity compared to wildtype cells due to low basal promotor activity.

FIG. 8: Expression of knock in target

Western blots show expression of recombinant human DNase I: Only transformed and induced cells (+) show strong signals due to anti-DNase I antibodies. The intracellular $PLA_1$-DNase-fusionprotein is visualized on the left blot by samples of cell lysates. Bands are running at higher molecular weight than the mature and processed positive control. On the right, supernatants were subjected to western blot; the size of the secreted protein of *Tetrahymena* argues for a correct processing when compared to the positive control.

FIG. 9: Overview reconstitution of DHFR-TS activity by knock in

Step I shows the constructs needed for homologous recombination of different exogenous DHFR-TS genes into the disrupted *Tetrahymena* DHFR-TS gene locus. The strain described in example 1 is transfected with these DNAs enabling selection by medium deficient of thymidine (step III). After allelic assortment stable cell-lines with different recombinant DHFR-TS properties are obtained (step IV) that can be used in antifolate drug screening.

FIG. 10: Enzyme (endogenous lipase) function of knock in target

Comparable to FIG. 6 the gene of an endogenous Ciliate-Lipase were combined with an inducible promoter and flanking regions of the *Tetrahymena* DHFR-TS gene. Subsequently the construct was integrated in a transformation vector (construct called pKOIX_M_Lipase) and transformed into *Tetrahymena*. After homologous integration of DHFR-TS construct into *Tetrahymena* DHFR-TS locus and following selection of the clones (comparable to the described procedure in FIG. 3-FIG. 6), supernatants of one clone transformed with pKOIX_M_Lipase were assayed for Lipase activity. Only cells, that have integrated pKOIX_M_Lipase construct, show high levels of Lipase activity. Wildtype cells show a low level of Lipase enzyme activity due to low promoter activity of the endogenous Lipase promoter. The lower graph shows the full-length integrative construct. FIG. 10 shows the Lipase activity in the supernatant of wildtype cells and induced transformants measured with a Lipase enzyme assay according to the Reflectoquant® lipase test instructions of the manufacturer.

Figure 11:
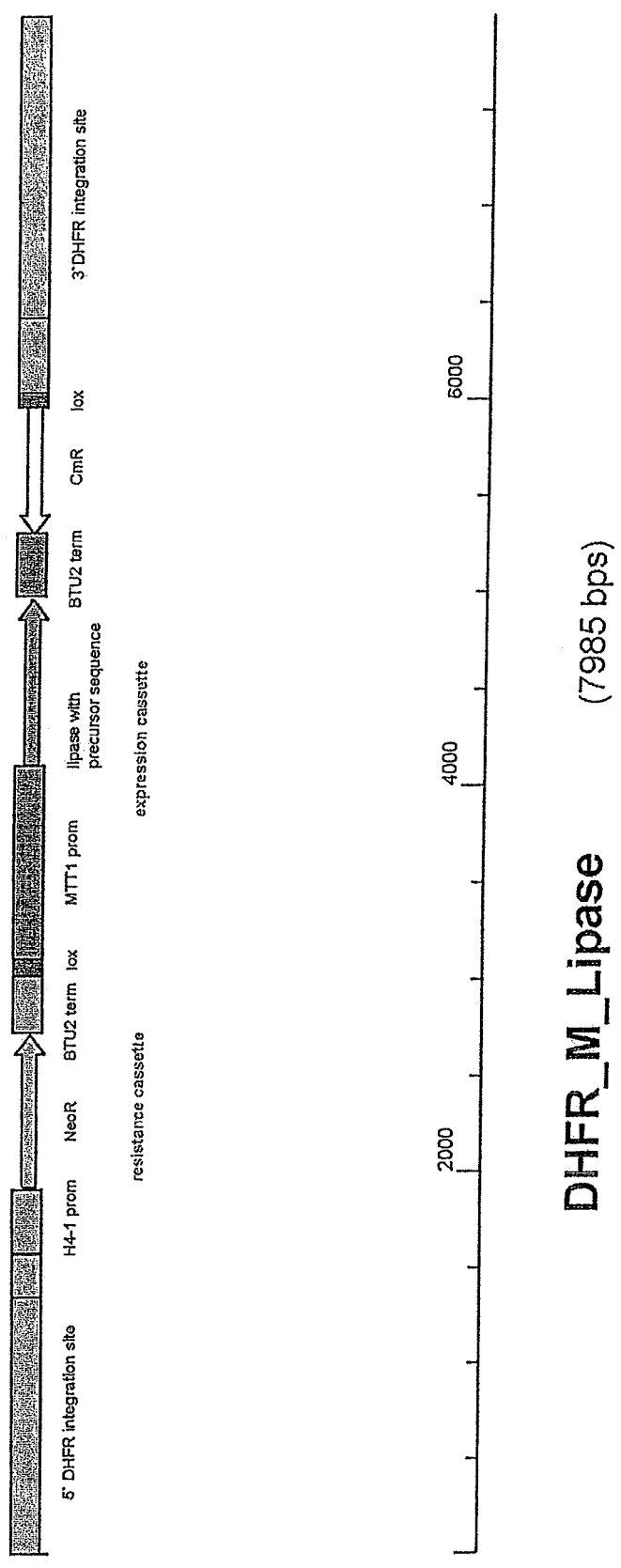

FIG. 11:

FIG. 11 shows the construction of the full-length integration/expression cassette for lipase (pKOIX_M_Lipase), which was transformed into *Tetrahymena* cells in order to obtain over-expression of endogenous Ciliate-Lipase.

EXAMPLES

The following examples are provided to illustrate the embodiments of the present invention, but are not intended to limit its scope.

Cells and Cell Culture

*Tetrahymena thermophila* strains B 1868.4, B 1868.7 and B 2068.1 were kindly provided by Peter J. Bruns and cultivated in skimmed milk medium (2% skimmed milk, 0.5% yeast extract, 0.1% ferrous sulphate chelate solution and 1% glucose) in SPP or in CDM medium.

Amplification of the DHFR-TS Gene of *T. Thermophila*

The DHFR-TS cDNA gene and its 5' and 3' flanking sites can be amplified using the following primer pairs. Nucleotides in small letters encode sites for restriction endonucleases.

Amplification of the DHFR-TS 5' flanking region:

```
                                          (SEQ ID NO: 4)
DHFR 5'1 F NotI: 5'-cccgcggccgcACAGAGTTAATGGAAAT
GGAGC-3', (SEQ ID NO: 5)
DHFR 5'2 R BamHI: 5'-ggggatccATATTTAAGCGATCTTTC
AATGG-3;
```

Amplification of the DHFR-TS cDNA and gene with introns:

```
                                          (SEQ ID NO: 6)
DHFR CDS F: 5'-cgcGAATTCATGAAAACAAGACATTTTGATATA
GTTTTAGC-3', (SEQ ID NO: 7)
DHFR CDS R: 5'-gcgCTCGAGTCAGACAGCCATTTTCATTTATAT
TTTAGGG-3',
```

Amplification of the DHFR-TS 3' flanking region:

```
                                          (SEQ ID NO: 8)
DHFR 3'1 F XhoI: 5'-gggctcgagATGCTCATGTTTACTCTAA
TCACG-3', (SEQ ID NO: 9)
DHFR 3'1 R Acc65I: 5'-gggggtaccAGTAAAAATAGAGTAGA
AGGAG-3'.
```

Construction of Plasmids

The pKOI (knock out/in) plasmid was constructed as follows: As backbone for selection and propagation in *E. coli* the pBS II SK plasmid was used. The 1.5 kb 5'-DHFR-TS integration site was amplified using the primer pair DHFR 5' 1 F NotI and DHFR 5' 2 R BamHI cloned into pBS II SK by using NotI and BamHI sites. Next the 1.4 kb paromomycin selection cassette from the pH4T2 (neo2) was cloned into the intermediate pBS IISK by BamHI and SmaI sites. Finally, the 3'-DHFR-TS integration site was amplified by primers DHFR 3' 1 F XhoI and DHFR 3' 1 R Acc65I and cloned by using the XhoI and Acc65I sites to finish the DHFR-TS knock out cassette.

The SacI site of the pBS II SK backbone had been destroyed by site directed mutagenesis to facilitate the use of the endogenous SacI site in the 3'-DHFR-TS integrating sequence and the XhoI site as unique cloning site in pKOI. These sites were used to insert cassettes for the expression of recombinant enzymes (knock in). In this study we used a human recombinant DNase I expression/secretion cassette and a Ciliate-endogenous lipase expression/secretion cassette. For DNase it consists of the first 115 aa of the endogenous PLA$_1$ precursor and the aa 23-281 of the mature human DNase I. To ensure proper translation of this fusion protein a codon optimised synthetic human DNase I gene was used. The expression was controlled by the previously described[6] inducible MTT-1 promotor, termination is regulated by the BTU2 terminator, like in the neo2 cassette of pH4T2[7].

Transformation of pKOI Plasmids (Biolistic Bombardment)

We used conjugating cells, as well as vegetative, growing and non-conjugating stationary T. thermophila strains. The transformation of the T. thermophila cells was performed as previously described by Gaertig et al[8].

Selection, Allelic Assortment and DHFR-TS Knock Out Assay

T. thermophila cell proliferation assay: For the first ca. 16 h after biolistic bombardment transformants were grown in skimmed milk medium. After that transformed cells were grown on SPP medium with in increasing concentrations of paromomycin (from 100 µg/mL to 1000 µg/mL) to support the allelic assortment process. After 3-4 weeks each clone was cultivated on CDM replica plates with or without thymidine (10 mg/mL). Functional DHFR-TS knock out clones are only able to grow in CDM medium supplemented with thymidine. The viability of the DHFR-TS knock out strains was monitored by determining the growth kinetic (FIG. 5).

The lack of the endogenous wildtype DHFR-TS gene in the MAC as well as the complete integration of the DHFR-TS knock out and rhDNase I knock in cassette was confirmed by PCR using the following primers:

```
                                          (SEQ ID NO: 10)
DHFR01F: 5'-CTTTTTAACAGCCTGCTGCTCG-3', (SEQ ID NO: 11)
DHFR02R: 5'-GATTTTGATGCTTCAATAAGGTTG-3', (SEQ ID NO: 12)
DHFR03F: 5'-TTATTTGTTTTATCATAGTGGAAAAGG-3', (SEQ ID NO: 13)
DHFR04R: 5'-CAGACACCTCAATCATATCAAAG-3', (SEQ ID NO: 14)
DHFR05F: 5'-GGTCCTCCATCAGATTGTGG-3'

(SEQ ID NO: 15)
DHFR06R: 5'-CGCGTCGAGTCAGACAGCCATTTTCATTTA-3'

(SEQ ID NO: 16)
Hex01F: 5'-ATGCAAAAGATACTTTTAATTACTTTC-3'

(SEQ ID NO: 17)
Hex02R: 5'-TATATTTTAGGAATGTTGTAATC-3'.
```

A pH4T2 plasmid carrying the same neo2 and DNase I expression/secretion cassettes was used a PCR control. The PCR strategy is illustrated in FIG. 6.

SDS-PAGE and Western Blot

Aliquots of transformed cells and of SPP supernatants were resuspended in sample buffer and separated on 15% SDS-PAGE. The gels were blotted onto nitrocellulose membranes and blocked in PBS containing 0.05% Tween 20 and 5% skim milk (PBS-TM). The expression of recombinant human DNase I in transformed Ciliates was detected by two specific anti sera from rabbit against human DNase I (antigen: recombinant human DNase I, Pulmozyme, Roche). Both sera detected the recombinant DNase I antigen. The serum was used in a 1:500 dilution in PBS-TM. After washing with PBS/T an HRP-conjugated anti rabbit serum was applied. The blots were developed by using chemiluminescence.

DNase I Activity Assay

The methyl green based DNase activity assay was performed as already published[9]. Samples were incubated at 37° C. for 24 h on a microtiter plate. Absorbance was measured at 620 nm. Calibration of the assay was achieved by different amounts of defined DNase I Units of Pulmozyme from Roche (CHO derived) in each experiment and linear regression. These results combined with semi-quantitative western blotting were used to calculate the specific activity of expressed DNase I.

Lipase Activity Assay

The Lipase activity assay (Reflectoquant® test strips together with the Reflectometer RQflex®) was performed according to the instructions of the manufacturer (VWR International GmbH, Hilpertstraβe 20a, 64295 Darmstadt, Germany, article number: 1.05851.0001).

Example 1

Generating Auxotrophic Heterokaryons

The protozoan T. thermophila belongs to the ciliates. These eukaryotes consist of two nuclei, a somatic macronucleus (MAC) and the genetic micronucleus (MIC). The MIC is the germline nucleus, i.e. it stores the genetic information for sexual progeny. The MIC is diploid and contains five pairs of chromosomes. In contrast to this the MAC is the somatic nucleus and no MAC DNA is transmitted to sexual progeny. The MAC contains 200-300 autonomously replicating pieces (ARP) that are derived from the MIC. Each of these units is present at about 45 copies except for the rDNA gene that is independently amplified to ca. 10000 copies per cell. The MAC DNA is the transcribed DNA and therefore responsible for the actual phenotype of T. thermophila cells.

It is obvious that genetic engineering ultimately needs the transformation of the functional MAC that is in charge of protein expression. The first approaches for heterologous expression were done by using plasmids that use the vast amplification of the rDNA gene during MAC development. However the episomal presence of these plasmids depends on the drug concentration and the plasmid may recombine homologously and non-directionally into endogenous rDNA units.

The more promising way is the stable transformation of cells. This means the stable integration of expression cassettes into the MAC and or/the MIC of T. thermophila. MIC transformation can be achieved by stably transforming the chromosomal DNA of the diploid MIC. After conjugation of two different mating types the old MACs of the conjugating cells disappear and new MACs were built in the progenies derived from the recombinant MICs that carry the new information. The whole process follows the statistics of the Mendelian genetics. The advantage of this approach is that one obtains stable clones that maintain the genetic properties and that can be crossed via classical genetics to combine various properties of different T. thermophila strains. This approach is very elaborative and time consuming. Furthermore, it was shown recently that scan RNAs derived from the old MAC play an important role in DNA elimination during the development of the somatic MAC from the germline MIC. The primary sequence of these small RNAs explains how the parental MAC epigenetically controls the genome rearrangement in the new MAC. In the case of stable MIC transformants this RNAi-like mechanism inhibits the establishment and maintenance of foreign expression cassettes in the developing new MAC.

Instead of episomal transformation by rDNA based plasmids or the stable transformation of the MIC a shortcut by the combination of stable MAC transformation with an immediate allelic assortment approach was used. This combination has several advantages. Firstly, the MAC transformation is much more efficient because there are at least about 45 potential integration sites per gene locus. Secondly, not only conjugating but also non-conjugating and therefore defined strains can be transformed. Finally, the recently reported genome rearrangements in the developing MAC that are regulated by scan RNA mechanisms can be short-circuited by MAC-transformation combined with allelic assortment.

To perform knock out/-in experiments the *T. thermophila* DHFR-TS gene and its flanking regions were amplified by using the primer pairs DHFR 5'1 F Not, DHFR 5'2 R BamHI for the 5' region non coding region, the primer pair DHFR 3'1 F XhoI: 5, DHFR 3'1 R Acc65I for the 3' region and the primers DHFR CDS F, DHFR CDS F for amplification of the coding region. The comparison of the coding region of the DHFR-TS structure gene to the DHFR-TS cDNA (amplified by the same DHFR CDS F/R primer pair) revealed the exon-intron architecture of the structure (FIG. 1).

To start the DHFR-TS knock out experiments the plasmid pKOI was constructed (FIG. 2). The neo2 cassette of pH4T2 was used to monitor the successful uptake of the plasmid by selection against paromomycin. The neo2 cassette of pKOI is flanked by the 1.5 kb fragments of the 5' and 3' region of the non-coding regions of the DHFR-TS gene, respectively (FIG. 2). Because pKOI lacks an appropriate origin of replication, paromomycin resistant *T. thermophila* clones argue for a proper homologous recombination event in the DHFR-TS gene locus. Nevertheless, the most convincing evidence for the correct integration into the DHFR-TS locus is a loss of the DHFR-TS activity in the transformed strain. In the case of ciliates this requires the all complete replacement of all chromosomal DHFR-TS wildtype alleles (~45 ARPs) by the ARPs that includes the knock out cassette. We achieved this by allelic assortment. This allelic or phenotypic assortment is based on randomised distribution of the MAC chromosomes units (ARPs) during mitosis. In order to force the assortment process into the desired direction—namely into the recombinant resistance gene—the transformed cells were cultivated for at least 2-3 weeks using increasing concentrations of the drug paromomycin. Single clones were isolated and tested for DHFR-TS deficiency by using a minimal chemical defined medium (CDM) with (+T) and without thymidine (−T). In FIG. 4 and FIG. 5 it is demonstrated that the found DHFR-TS knock out clones are real auxotrophic strains: The mutants are able to grow in CDM with thymidine like wildtype strains or strains with an incomplete allelic assortment. In CDM lacking thymidine they are unable to grow (see FIG. 4 and FIG. 5).

Example 2

Knock Out DHFR-TS to Knock in the Gene of Interest

The knock out of the endogenous DHFR-TS gene of *T. thermophila* also provides the possibility to knock in a further foreign gene that can be expressed heterologously in the DHFR-TS knock out strains. For this purpose the pKOI $D_{VL}$ plasmid was constructed. It consists of a pKOI backbone with an additional expression cassette that encodes the first 115 amino acids (aa) of the precursor sequence of the $PLA_1$ gene and the mature human DNase I (amino acids 23 to 281). Construct for the expression of the endogenous lipase contains the endogenous-Ciliate-lipase-prepro peptide sequence and the mature endogenous Ciliate-lipase.

The $PLA_1$ prepro peptide (aa 1 to 110) has significant similarity to members of the cathepsin L family and mediates secretion into the medium. Similar to $PLA_1$ prepro peptide the endogenous-Ciliate-lipase prepro peptide mediates the secretion of the lipase into the medium.

In the case of the DNase the five additional amino acids (aa 111 to 115) should ensure an optimal cleavage of the pro $PLA_1$-DNase I fusion protein by endogenous pro-peptidases. In contrast to the neo2 cassette the expression of the ppPLA115-DNase I fusion protein is regulated by the inducible MTT1 promotor. The inducible system was selected because it allows a clear discrimination between the DNase activity of heterologously expressed recombinant human DNase I and the basal activity due to at least two endogenous DNases. According to this the inducible system was also selected in the case of Lipase because it allows a clear discrimination between the basal level of the endogenous Lipase activity and homologous overexpressed endogenous Lipase activity. The transformation, selection of positive clones and the directed allelic assortment were done as outlined in example 1. Furthermore, the correct and complete integration of both expression cassettes (neo2 and the DNase I) in the DHFR-TS locus was tested by a PCR approach. FIG. 6 shows that this is the case.

In order to demonstrate the pKOI concept, cells of these DHFR-TS knock out strains carrying the $ppPLA_{115}$-DNase expression cassette were treated with and without Cadmium. Only induced strains showed an elevated DNase activity in the supernatant (FIG. 7). To confirm this enzymatic data a specific antiserum against human DNase I was used to analyse the cell extracts and the supernatant of these human DNase expressing DHFR-TS knock out strains by western blot. The results illustrate that the DHFR-TS knock out strains are capable of expressing and secreting the functional recombinant human protein (FIG. 8).

Example 3

Recombinant Reconstitution of DHFR-TS Activity to Create Strains for High Throughput Antifolate Screening The reconstitution of the DHFR-TS activity in DHFR-TS deficient *Tetrahymena* strains can be done by heterologously expressing bifunctional DHFR-TS enzymes of other Alveolata. As already mentioned in the introduction, this phylogenetic group consists of the *Ciliata*, Dinoflagellata and Apicomplexa/Sporozoa. Especially the Apicomplexa are of high medical interest because all members are intracellular parasites and some of them cause very severe diseases (malaria, toxoplasmosis, cryptosporidiosis).

Apart from the fact that DHFR-TS deficient *T. thermophila* strains in combination with a DHFR-TS plasmid/vector provide a new marker for molecular biology, the same system can be used to generate defined test strains for drug development applications. Due to the close phylogenetic relationship it is also possible to recover the DHFR-TS activity in deficient *Tetrahymena* strains by DHFR-TS enzymes from other members of the Alveolata group. This implies the application of DHFR-TS deficient *T. thermophila* strains in searching for and testing novel anti DHFR-TS drugs (antifolates). This is of very high importance because antifolates have been one of the most promising drugs in the fight against malaria. The fact that anti DHFR-TS drugs have been administered for a long time in e.g. malaria patients is the reason that during the last decades many of the parasites became resistant. At present many approaches are being explored to find new and more specific and efficient drugs against the parasite DHFR-TS enzyme. As the search for new antifolates relies on structure determination using NMR and crystallization techniques, most of these approaches are very time and cost intensive.

DHFR-TS deficient *T. thermophila* strains that express an active parasite DHFR-TS will not only be able to grow in medium lacking thymidine, but they are also suitable to search for novel antifolates. Thus the DHFR-TS deficient strains recovered by the homologous bienzyme of the parasites represent a simple and flexible in vivo test system conferrable to other disease causing parasites of the Apicomplexa group. For example antifolates against *Plasmodium vivax* strains have not been considered because no appropriate and flexible in vivo system for high throughput approaches was available. This can be done easily by recovering the DHFR-TS activity of *T. thermophila* strains by using the homologous bienzymes of *Plasmodium vivax, Plasmodium malariae, Plasmodium ovale* as well as enzymes from Apicomplexa/ Sporozoa that cause toxoplasmosis or cryptosporidiosis. FIG. 9 illustrates this concept. The DHFR-TS enzyme of the pyrimethamine-sensitive *Plasmodium falciparum* strain 3D7 was used to recover the DHFR-TS activity in a *T. thermophila* strain, lacking DHFR-TS activity. In parallel a DHFR-TS from a *Plasmodium falciparum* strain that is resistant against the pyrimethamine treatment (for example the DHFR-TS S108N mutant) is tested. By measuring the effect of pyrimethamine in dose response curves on the two different transformands drug resistance and sensitivity can be determined easily. Subsequently new potential drugs can be added to the medium to show effectiveness on yet resistant DHFR-TS mutants.

REFERENCE LIST

1. Gaertig, J., Thatcher, T. H., Gu, L. & Gorovsky, M. A. Electroporation-mediated replacement of a positively and negatively selectable beta-tubulin gene in *Tetrahymena thermophila. Proc. Natl. Acad. Sci. U.S.A.* 91, 4549-4553 (1994).
2. Garrett, C. E. et al. A bifunctional thymidylate synthetase-dihydrofolate reductase in protozoa. *Mol. Biochem. Parasitol.* 11, 257-265 (1984).
3. Kotsifaki, H., Kapoulas, V. & Deliconstantinos, G. Targeting of liposomes containing methotrexate towards *Tetrahymena pyriformis* cells. *Gen. Pharmacol.* 16, 573-577 (1985).
4. Stechmann, A. & Cavalier-Smith, T. Rooting the eukaryote tree by using a derived gene fusion. *Science* 297, 89-91 (2002).
5. Hastings, M. D. & Sibley, C. H. Pyrimethamine and WR99210 exert opposing selection on dihydrofolate reductase from *Plasmodium vivax. Proc. Natl. Acad. Sci. U.S. A* 99, 13137-13141 (2002).
6. Shang, Y. et al. A robust inducible-repressible promoter greatly facilitates gene knockouts, conditional expression, and overexpression of homologous and heterologous genes in *Tetrahymena thermophila. Proc. Natl. Acad. Sci. U.S. A* 99, 3734-3739 (2002).
7. Gaertig, J., Gu, L., Hai, B. & Gorovsky, M. A. High frequency vector-mediated transformation and gene replacement in *Tetrahymena. Nucleic Acids Res.* 22, 5391-5398 (1994).
8. Gaertig, J. & Gorovsky, M. A. DNA-mediated transformation in *Tetrahymena. Methods Cell Biol.* 47, 559-569 (1995).
9. Sinicropi, D., Baker, D. L., Prince, W. S., Shiffer, K. & Shak, S. Colorimetric determination of DNase I activity with a DNA-methyl green substrate. *Anal. Biochem.* 222, 351-358 (1994).

The invention claimed is:

1. An isolated nucleic acid having the nucleotide sequence according to SEQ ID NO: 1 and coding for a protein having dihydrofolate reductase and thymidylate synthase (DHFR-TS) activity.

2. A method for producing a ciliate cell having reduced dihydrofolate reductase (DHFR) activity, reduced thymidylate synthase (TS) activity, or reduced DHFR-TS activity, comprising the steps of a) transforming the ciliate cell by inserting a construct into at least one of the endogenous DHFR-TS genes of the ciliate cell macronucleus (MAC), wherein said at least one endogenous DHFR-TS gene comprises SEQ ID NO: 1, and wherein said construct contains an allele that disrupts said endogenous DHFR-TS gene, b) inducing an allelic assortment process in the transformed ciliate cell to generate ciliate cells having the construct inserted in most or all endogenous DHFR-TS genes of the MAC of said ciliate cells, c) cultivating the ciliate cells generated in step b) with an without thymidine, and
d) identifying ciliate cells from step c) which do not grow without thymidine, wherein ciliate cells which do not grow without thymidine are ciliate cells having reduced DHFR activity, TS activity, or reduced DHFR-TS activity.

3. A method for producing a ciliate cell having reduced DHFR activity, reduced TS activity, or DHFR-TS activity, comprising the steps of:
   a) transforming the ciliate cell by inserting a construct into at least one of the endogenous DHFR-TS genes of the ciliate cell micronucleus (MIC), wherein said at least one endogenous DHFR-TS gene comprises SEQ ID NO:1, and wherein said construct contains an allele that disrupts said endogenous DHFR-TS gene,
   b) breeding the ciliate cell of step a) with other ciliate cells to produce ciliate cells that contains a new MAC derived from the altered MIC of step a), wherein the ciliate cells that contain the new MAC have the construct inserted in most or all endogenous DHFR-TS genes of the MAC,
   c) cultivating the ciliate cells generated in step b) with and without thymidine, and
   d) identifying ciliate cells from step c) which do not grow without thymidine, wherein ciliate cells which do not grow without thymidine are ciliate cells having reduced DHFR activity, TS activity, or reduced DHFR-TS activity.

4. The method according to claim 2, wherein the ciliate cell is a *Tetrahymena* cell.

5. The method according to claim 2, wherein the ciliate cell is a *Tetrahymena thermophila* cell.

6. The method according to claim 2, wherein the regions 1.5 kb upstream and 1.5 kb downstream from the endogenous gene comprising SEQ ID NO: 1 are altered.

7. A method for expressing a non-endogenous DHFR-TS protein in a ciliate cell, wherein said method comprises the steps of:
   a) transforming the ciliate cell by inserting a construct into at least one of the endogenous DHFR-TS genes of the ciliate cell macronucleus (MAC), wherein said at least one endogenous DHFR-TS gene comprises SEQ ID NO: 1, and wherein said construct contains an allele that disrupts said endogenous DHFR-TS gene,
   b) inducing an allelic assortment process in the transformed ciliate cell to generate ciliate cells having the construct inserted in most or all endogenous DHFR-TS genes of the MAC of said ciliate cells,
   c) cultivating the ciliate cells generated in step b) with and without thymidine,
   d) identifying ciliate cells from step c) which do not grow without thymidine, wherein ciliate cells which do not grow without thymidine are ciliate cells having reduced DHFR activity, TS activity, or reduced DHFR-TS activity, and
   e) transfecting the ciliate cells identified in step d) with a DNA or RNA molecule coding for a non-endogenous DHFR-TS protein to express a non-endogenous DHFR-TS protein in the ciliate cell.

8. The method according to claim 7, wherein the DNA or RNA molecule coding for the non-endogenous DHFR-TS protein is derived from an alveolate.

9. The method according to claim 7, wherein the DNA or RNA molecule coding for the non-endogenous DHFR-TS protein is derived from a ciliate.

10. The method according to claim 7, wherein the DNA or RNA molecule coding for the non-endogenous DHFR-TS protein is derived from *Tetrahymena*.

11. The method according to claim 7, wherein the DNA or RNA molecule coding for the non-endogenous DHFR-TS protein is derived from an apicomplexan.

* * * * *